(12) United States Patent
Beeley et al.

(10) Patent No.: US 8,263,550 B2
(45) Date of Patent: *Sep. 11, 2012

(54) EXENDIN AGONIST COMPOUNDS

(75) Inventors: Nigel Robert Arnold Beeley, San Diego, CA (US); Kathryn S. Prickett, Foster City, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/959,176

(22) Filed: Dec. 2, 2010

(65) Prior Publication Data

US 2011/0071076 A1    Mar. 24, 2011

Related U.S. Application Data

(62) Division of application No. 11/511,738, filed on Aug. 28, 2006, now Pat. No. 7,858,740, which is a division of application No. 10/181,102, filed as application No. PCT/US98/16387 on Aug. 6, 1998, now Pat. No. 7,157,555.

(60) Provisional application No. 60/055,404, filed on Aug. 8, 1997.

(51) Int. Cl.
*A61K 38/28* (2006.01)
*A61K 38/22* (2006.01)
*C07K 14/605* (2006.01)
*C07K 14/435* (2006.01)

(52) U.S. Cl. ........ 514/4.8; 514/11.7; 514/21.3; 514/6.9; 530/324

(58) Field of Classification Search .................. None
See application file for complete search history.

(56) References Cited

U.S. PATENT DOCUMENTS

| | | | |
|---|---|---|---|
| 5,118,666 A | 6/1992 | Habener | |
| 5,120,712 A | 6/1992 | Habener | |
| 5,424,286 A | 6/1995 | Eng | |
| 5,512,549 A | 4/1996 | Chen | |
| 5,545,618 A | 8/1996 | Buckley et al. | |
| 5,574,008 A | 11/1996 | Johnson et al. | |
| 5,686,511 A | 11/1997 | Bobo | |
| 5,705,483 A | 1/1998 | Galloway et al. | |
| 5,846,937 A | 12/1998 | Drucker | |
| 5,981,488 A | 11/1999 | Hoffmann | |
| 6,191,102 B1 | 2/2001 | DiMarchi et al. | |
| 6,268,343 B1 | 7/2001 | Knudsen et al. | |
| 6,767,887 B1 | 7/2004 | Hoffmann et al. | |
| 2008/0124347 A1 | 5/2008 | Kim et al. | |

FOREIGN PATENT DOCUMENTS

| | | |
|---|---|---|
| WO | WO 90/11296 | 10/1990 |
| WO | WO 91/11457 | 8/1991 |
| WO | WO 93/18786 | 9/1993 |
| WO | WO 93/25579 | 12/1993 |
| WO | WO 98/05351 | 2/1998 |
| WO | WO 98/19698 | 5/1998 |
| WO | WO 98/30231 | 7/1998 |
| WO | WO 99/07404 | 2/1999 |

OTHER PUBLICATIONS

EPO Communication re Notice of Opposition to EP 1032587 filed Oct. 2008.
EPO Communication re Notice of Opposition and Opposition to EP 1019077 by Strawman Lijmited (EPO Comm dated Sep. 5, 2008).
EPO Communication re Notice of Opposition to EP 1066314, filed Sep. 2008.
Adelhorst et al., *J.Biol.Chem.* 269(9):6275-8 (1994): Structure-activity studies of glucagon-like peptide-1 (GLP-1).
Alcantara et al.., *Archives of Biochem. Biophys.* 341(1):1-7 (1997): Exendin-4 Agonist and Exendin(9-39) amide Agonist of the GLP-1(7-36) amide Effects in Liver and Muscle.
Ashkenazi et al., *PNAS USA* 87:7150-7154 (1990): Mapping the CD4 binding site for human immunodeficiency virus by alanine-scanning and mutagenesis.
Bachem internet website k(product U-1160, downloaded Dec. 13, 2007.
Bartlett et al., *Bioorg.Chem.* 14:356-377 (1986): Inhibition of Chymotrypsin by Phosphonate and Phosphonamidate Peptide Analogs.
Bhavsar, *Soc. Neurosci. Abst.* 21:460 (188.8) (1995): Inhibition of Gastric Emptying and of Food Intake Appear to be Independently Controlled in Rodents.
Byrne et al., *Diab. Med.* 13(1):854-860 (1996): Human Studies with Glucagon-Like Peptide-1: Potential of the Gut Hormone for Clinical Uses.
Chen & Drucker, *J. Biol. Chem.* 272(7):4108-4115 (Feb. 14, 1997): Tissue-Specific Expression of Unique mRNAs that Encode Proglucagon-derived Peptides or Exendin-4 in the Lizard.
Conn & Stumpf, *Outlines in Biochemistry*, Third Edition, John Wiley & Sons, pp. 69-74 (1972): Amino Acids and Proteins.
Copley et al., *Curr. Drug Metab.* 7:1-8 (2006): Investigation of Exenatide Elimination and its in Vivo and in Vitro Degradation.
Cunningham & Wells, *Science* 244:1081-1085 (1989): High-Resultion Epitope mapping of hGH-Receptor Interactions by alanine-Scanning Mutagenesis.
D'Alessio et al., *J.Clin.Invest.* 97:133-38 (1996): Elimination of the Action of Glucaton-Like Peptide-1 Causes an Impairment of Glucose Tolerance after Nutrietn ingestion by Healthy Baboons.
Dupre et al., *Diabetes* 44:626-620 (1995): Glucagon-Like Peptide-1 Reduces Postprandial Glycemic Excursions in IDDM.
Eissele et al., *Life Sci.* 55(8):629-34 (1994): Rat Gastric Somatostatin and Gastrin Release: Interactions of Exendin-4 and Truncated Glucagon-Like Peptide-1 (GLP-1) Amide.

(Continued)

*Primary Examiner* — Michael Borin
(74) *Attorney, Agent, or Firm* — Amylin Pharmaceuticals, Inc.

(57) ABSTRACT

Novel exendin agonist compounds are provided. These compounds are useful in treating Type I and II diabetes and conditions which would benefit by lower plasma glucose and delaying and/or slowing gastric emptying.

10 Claims, 7 Drawing Sheets

OTHER PUBLICATIONS

Eng et al., *J. Biol. Chem.* 265:20259-62 (1990): Purification and Structure of Exendin-3, a New Pancreatic Secretagogue Isolated from Heloderma horridum Venom.

Eng et al., *J. Biol. Chem.* 267:7402-05 (1992): Isolation and Characterization of Exendin-4, an Exendin-3 Analogue, from heloderma suspectum venom.

Fehmann et al., *Peptides* 15(3):453-6 (1994): Stable Expression of the Rat GLP-1 Receptor in CHO Cells: Activation and Binding Characteristics Utilizing GLP-1(7-36)-Amide, oxyntomodulin, Exendin-4 and Exendin(9-39).

Ferguson et al., *Annu. Rev. Biochem.* 57:285-320 (1988): Cell-Surface Anchoring of Proteins via Glycosylphosphatidylinositol Structures.

Gibbs & Zoller, *J. Biol. Chem.* 266(14):8923-8931 (1991): Rational Scanning Mutagenesis of a Protein Kinase Identifies Functional Regions Involved in Catalysis and Substrate Interactions.

Goke et al., *J. Biol. Chem.* 268:19650-55 (1993): Exendin-4 is a High Potency Agonist and Truncated Exendin-(9-36)-amide an Antagonist at the Glucagon-like Peptide 1-(7-36)-amide Receptor of Insulin secreting Beta Cells.

Goldstone et al., *FEBS Letters* 415:134-138 (1997): Leptin interacts with Glucagon-Like Peptide-1 Neurons to Reduce Food Intake and Body Weight in Rodents.

Gutniak et al., *NEJM* 326:1316-1322 (1992): Antidiabetogenic Effect of Glucagon-Like Peptide-1 (7-36) Amide in Normal Subjects and Patients with Diabetes Mellitus.

Halaas et al., *Science* 269:543-546 (1995): Weight-Reducing Effects of the Plasma Protein Encoded by the Obese Gene.

Harris, *Gut* Suppl. 3,:S1-S4 (1994): Somatostatin and somatostatin analogues, pharmacokinetics and pmarmacodynamic effects.

Hunt & Ramsbottom, *Brit. Med. J.* 4(5576):386-387 (1967): Effect of Gastrin II on Gastric Emptying and Secretion During a Test Meal.

Kodama et al., *Diabetes Care* 13(11):1109-1111 (1990): Effect of Captopril on Glucose Concentration Possible Role of Augmented Postprandial Forearm Blood Flow.

Kolligs et al., *Diabetes* 44:16-19 (1995): Reduction of the incretin Effect in Rats by the Glucagon-Like Peptide-1 Receptor Antagonist Exendin (9-39) Amide.

Lawler et al., *Gastroenterology* 112(4 Suppl):A194 XP 002167251 (1997): Comparison of effects of Amylin, glucagon-like peptide-1 (GLP-1) and Exendin-4 to inhibit pentagastrin-stimulated gastric acid secretion in rats.

Leibel et al., *NEJM.* 332(10):621-628 (1995): Changes in Energy Expenditure Resulting from Altered Body Weight.

Lithell et al., *J. Cardiovasc. Pharmacol.* 15(Supp. 5):S46-S52 (1990): Insulin Sensitvity in Newly Detected Hypertensive Patients: Influence of Captopril and Other Antihypertensive Agents on Insulin Sensitivity and Related Biological Parameters.

Malhotra et al., *Regul. Peptides* 41:149-56 (1992): Exendin-4, a New Peptide from Heloderma suspectum Venom, Potentiates Cholecystokinin-induced Amylase Release from Rat Pancreatic Acini.

Montrose-Rafizadeh et al., *Diabetes* 45(Suppl. 2):152A (1996): Structure-function Analysis of Exendin-4 / GLP-1 Analogs.

Nauck et al., *J. Clin. Invest.* 91:301-307 (1993): Preserved Incretin Activity of Glucaton-like Peptide-1 (7-36 Amide) but not of Synthetic Human Gastric Inhibitory Polypeptide in Patients with Type 2 Diabetes Mellitus.

Nauck, *Diabetic Med.* 13(9 Supp 5):S39-S43 (1996): Therapeutic Potential of Glucagon-Like Petpide 1 in Type 2 Diabetes.

Navarro et al., *J. Neurochem.* 67:1982-1991 (1996): Colocalization of Glucagon-Like Peptide-1 (GLP-1) Receptors, Glucose Transporter GLUT-2, and Glucokinase mRNAs in Rat Hypothalamic Cells: Evidence for a Role of GLP-1 Receptor Agonists as an Inhibitory Signal for Food and Water Intake.

Neidigh et al., *Biochemistry* 40(44):13188-13200 (2001): Exendin-4 and Glucagon-like Peptide-1: NMR Structural Comparison in the Solution and Micelle-Associated States.

Nielsen & Baron, *Curr. Opin. Invest. Drugs* 4(4):401-405 (2003): Pharmacology of Exenatide (synthetic Exendin-4) for the treatment of type 2 diabetes.

Nielsen et al., *Regul. Peptides* 117:77-88 (2004): Pharmacology of exenatide (synthetic Exendin-4): A potential therapeutic for improved glycemic control of type 2 diabetes.

O'Halloran et al., *J. Endocrinol.* 126(1):169-73 (1990): Glucagon-Like Peptide-1 (7-36-NH2): A Physiological Inhibitor of Gastric Acid Secretion in Man.

Orskov et al., *Diabetes* 42:658-61 (1993): Biological Effects and Metabolic Rates of Glucagonlike Peptide-1-7-36 amide and Glucagonlike Peptide-1-7-37 in Healthy Subjects are indistinguishable.

Pelleymounter et al., *Science* 269:540-543 (1995): Effects of the Obese Gene Product on Body Weight Regulation in ob/ob Mice.

Raufman et al., *J. Biol. Chem.* 266:2897-902 (1991): Exendin-3, a Novel Peptide from Heloderma horridum venom, interacts with vasoactive intestinal peptide receptors and a newly described receptor on dispersed acini from Guinea Pig Pancreas.

Raufman et al., *J. Biol. Chem.* 267:21432-37 (1992): Truncated Glucagon-like Peptide-1 Interacts with Exendin Receptors in Dispersed Acini from guinea Pig Pancreas.

Schepp et al., *Eur. J. Pharm.* 269:183-91 (1994): Exendin-4 and Exendin-(9-39)NH2: Agonist and Antagonist, Respectively, at the Rat parietal Cell Receptor for Glucagon-like Peptide-1-(7-36)NH2.

Schjoldager et al., *Dig. Dis. Sci.* 34(5):703-8 (1989): GLP-1 (Glucagon-like Peptide 1) and Truncated GLP-1, Fragments of Human Proglucagon, Inhibit Gastric Acid Secretion in Humans.

Singh et al., *Regul. Peptides* 53:47-59 (1994): Use of 125I-[Y39]Exendin-4 to Characterize Exendin Receptors on Dispersed Pancreatic Acini and Gastric Chief Cells from Guinea Pigs.

Thorens et al., *Diabetes* 42(11):1678-82 (1993): Cloning and Functional Expression of the Human Islet GLP-1 Receptor.

Thorens, *PNAS USA* 89:8641-45 (1992): Expression Cloning of the Pancreatic B-Cell Receptor for the Gluco-Incretin Hormone Glucagon-like Peptide 1.

Turton et al., *Nature* 379:69-73 (1996): A Role for Glucagon-Like Peptide-1 in the Central Regulation of Feeding.

Veale et al., *Eur. J. Pharm.* 262:133-141 (1994): The Presence of islet Amyloid Polypeptide/Calcitonin Gen-Related Peptide/Salmon Calcitonin Binding Sites in the Rat Nucleus Accumbens.

Wang et al., *J. Clin. Invest.* 95:417-21 (1995): Glucagon-like Peptide-1 is a Physiological Incretin in Rats.

Watson et al., *Curr. Med. Res. Opin* 12(6):374-78 (1991): Effects of Captopril on Glucose tolerance in Elderly Patients with Congestive Cardiac Failure.

Weir, *J. Clin. Invest.* 95:1 (1995): Glucagon-Like Peptide-1 (GLP-1): A Piece of the Incretin Puzzle.

Wettergren et al., *Dig. Dis. Sci.* 38(4):665-73 (1993): Truncated GLP-1 (Proglucagon 78-107-Amide) Inhibits Gastric and Pancreatic Functions in Man.

Willms et al., *J. Clin. Endocrinol. Metab.* 81(1):327-32 (1996): Gastric Emptying, Glucose Responses, and Insulin Secretion after a Liquid Test Meal: Effects of Exogenous Glucagon-Like Peptide-1 (GLP-1)-(7-36) Amide in Type 2 (Noninsulin-Dependent) Diabetic Patients.

Young et al., *Program and Abstracts*, 105th Int'l Congress of Endocrinology, Jun. 12-15, 1996, San Francisco, CA p. 419 (P2-58), Abstract.

| Compound [SEQ. ID. NO.] | Xaa$_1$ | Xaa$_2$ | Xaa$_3$ | Xaa$_4$ | Xaa$_5$ | Xaa$_6$ | Xaa$_7$ | Xaa$_8$ | Xaa$_9$ | Xaa$_{10}$ |
|---|---|---|---|---|---|---|---|---|---|---|
| 1(3129)[5] | His | Gly | Glu | Phe | Thr | Ser | Asp | Leu | Leu | Phe |
| 2(3174)[6] | His | Gly | Glu | Phe | Thr | Ser | Asp | Leu | Leu | Phe |
| 3(3175)[7] | His | Gly | Glu | Phe | Thr | Ser | Asp | Leu | Met | Phe |
| 4(3110)[8] | Tyr | Gly | Glu | Phe | Thr | Ser | Asp | Leu | Met | Phe |
| 5(3000)[9] | His | Gly | Glu | Phe | Thr | Ser | Asp | Leu | Met | Phe |
| 6 [10] | His | Gly | Asp | Phe | Thr | Ser | Asp | Leu | Met | Phe |
| 7 [11] | His | Gly | Glu | naph | Thr | Ser | Asp | Leu | Met | Phe |
| 8 [12] | His | Gly | Glu | Phe | Ser | Thr | Asp | Leu | Met | Phe |
| 9 [13] | His | Gly | Glu | Phe | Ser | Thr | Asp | Leu | Met | Phe |
| 10 [14] | His | Gly | Glu | Phe | Thr | Ser | Glu | Leu | Met | Phe |
| 11 [15] | His | Gly | Glu | Phe | Thr | Ser | Asp | Leu | Met | Phe |
| 12 [16] | His | Gly | Glu | Phe | Thr | Ser | Asp | pGly | Met | Phe |
| 13 [17] | His | Gly | Glu | Phe | Thr | Ser | Asp | pGly | Leu | Phe |
| 14 [18] | His | Gly | Glu | Phe | Thr | Ser | Asp | Leu | pGly | Phe |

| Fig. 1A | Fig. 1B |

| Xaa11 | Xaa12 | Xaa13 | Xaa14 | Xaa15 | Xaa16 | Xaa17 | Xaa18 | Z |
|---|---|---|---|---|---|---|---|---|
| Ile | Glu | Phe | Pro | Pro | Pro | Pro | Ser | NH2 |
| Ile | Glu | Trp | Pro | Pro | Pro | Pro | Ser | NH2 |
| Ile | Glu | Phe | Pro | Pro | Pro | Pro | Ser | NH2 |
| Ile | Glu | Trp | Pro | Pro | Pro | Pro | Ser | NH2 |
| Ile | Glu | Trp | Pro | Pro | Pro | Pro | Tyr | NH2 |
| Ile | Glu | Trp | Pro | Pro | Pro | Pro | Ser | NH2 |
| Ile | Glu | Trp | Pro | Pro | Pro | Pro | Ser | NH2 |
| Ile | Glu | Trp | Pro | Pro | Pro | Pro | Ser | NH2 |
| Ile | Glu | Trp | Pro | Pro | Pro | Pro | Ser | NH2 |
| Ile | Glu | Trp | Pro | Pro | Pro | Pro | Ser | NH2 |
| Ile | Glu | Trp | Pro | Pro | Pro | Pro | Ser | NH2 |
| Ile | Glu | Phe | Pro | Pro | Pro | Pro | Ser | NH2 |
| Ile | Glu | Trp | Pro | Pro | Pro | Pro | Ser | NH2 |

*Fig. 1B*

| Compound [SEQ. ID. NO.] | Xaa$_1$ | Xaa$_2$ | Xaa$_3$ | Xaa$_4$ | Xaa$_5$ | Xaa$_6$ | Xaa$_7$ | Xaa$_8$ | Xaa$_9$ | Xaa$_{10}$ |
|---|---|---|---|---|---|---|---|---|---|---|
| 15 [19] | His | Gly | Glu | Phe | Thr | Ser | Asp | Leu | pGly | Phe |
| 16 [20] | His | Gly | Glu | Phe | Thr | Ser | Asp | Leu | Met | naph |
| 17 [21] | His | Gly | Glu | Phe | Thr | Ser | Asp | Leu | Met | Phe |
| 18 [22] | His | Gly | Glu | Phe | Thr | Ser | Asp | Leu | Leu | Phe |
| 19 [23] | His | Gly | Glu | Phe | Thr | Ser | Asp | Leu | Met | Phe |
| 20 [24] | His | Gly | Glu | Phe | Thr | Ser | Asp | Leu | Leu | Phe |
| 21 [25] | His | Gly | Glu | Phe | Thr | Ser | Asp | Leu | Met | Phe |
| 22 [26] | His | Gly | Glu | Phe | Thr | Ser | Asp | Leu | Met | Phe |
| 23 [27] | His | Gly | Glu | Phe | Thr | Ser | Asp | Leu | Met | Phe |
| 24 [28] | His | Gly | Glu | Phe | Thr | Ser | Asp | Leu | Met | Phe |
| 25 [29] | His | Gly | Glu | Phe | Thr | Ser | Asp | Leu | Met | Phe |
| 26 [30] | His | Gly | Glu | Phe | Thr | Ser | Asp | Leu | Met | Phe |
| 27 [31] | His | Gly | Glu | Phe | Thr | Ser | Asp | Leu | Leu | Phe |
| 28 [32] | His | Gly | Glu | Phe | Thr | Ser | Asp | Leu | Leu | Phe |
| 29 [33] | His | Gly | Glu | Phe | Thr | Ser | Asp | Leu | Met | Phe |
| 30 [34] | His | Gly | Glu | Phe | Thr | Ser | Asp | Leu | Met | Phe |
| 31 [35] | His | Gly | Glu | Phe | Thr | Ser | Asp | Leu | Leu | Phe |

*Fig. 1C*

| Fig. 1D | Fig. 1E |
|---|---|

*Fig. 1D*

| Xaa11 | Xaa12 | Xaa13 | Xaa14 | Xaa15 | Xaa16 | Xaa17 | Xaa18 | Z |
|---|---|---|---|---|---|---|---|---|
| Ile | Glu | Phe | Pro | Pro | Pro | Pro | Ser | NH2 |
| Ile | Glu | Trp | Pro | Pro | Pro | Pro | Ser | NH2 |
| Val | Glu | Trp | Pro | Pro | Pro | Pro | Ser | NH2 |
| Val | Glu | Phe | Pro | Pro | Pro | Pro | Ser | NH2 |
| tBuG | Glu | Trp | Pro | Pro | Pro | Pro | Ser | NH2 |
| tBuG | Glu | Phe | Pro | Pro | Pro | Pro | Ser | NH2 |
| Ile | Asp | Trp | Pro | Pro | Pro | Pro | Ser | NH2 |
| Ile | Glu | Phe | Pro | Pro | Pro | Pro | Ser | NH2 |
| Ile | Glu | Trp | tPro | tPro | tPro | tPro | Ser | NH2 |
| Ile | Glu | Trp | Pro | tPro | tPro | tPro | Ser | NH2 |
| Ile | Glu | Trp | hPro | hPro | hPro | hPro | Ser | NH2 |
| Ile | Glu | Trp | Pro | hPro | hPro | hPro | Ser | NH2 |
| Ile | Glu | Trp | tPro | tPro | tPro | tPro | Ser | NH2 |
| Ile | Glu | Phe | hPro | hPro | hPro | hPro | Ser | NH2 |
| Ile | Glu | Phe | MeAla | MeAla | MeAla | MeAla | Ser | NH2 |
| Ile | Glu | Trp | Pro | MeAla | MeAla | MeAla | Ser | NH2 |
| Ile | Glu | Phe | MeAla | MeAla | MeAla | MeAla | Ser | NH2 |

*Fig. 1E*

His Ser Asp Gly Thr Phe Thr Ser Asp Leu Ser Lys Gln Met Glu Glu
1           5                   10              15
Glu Ala Val Arg Leu Phe Ile Glu Trp Leu Lys Asn Gly Gly Pro Ser
            20                  25                  30
Ser Gly Ala Pro Pro Pro Ser-NH₂
            35

Fig. 2

His Gly Glu Gly Thr Phe Thr Ser Asp Leu Ser Lys Gln Met Glu Glu
1           5                   10              15
Glu Ala Val Arg Leu Phe Ile Glu Trp Leu Lys Asn Gly Gly Pro Ser
            20                  25                  30
Ser Gly Ala Pro Pro Pro Ser-NH₂
            35

Fig. 3

His Ala Glu Gly Thr Phe Thr Ser Asp Val Ser Ser Tyr Leu Glu Gly
            5                   10              15
Gln Ala Ala Lys Glu Phe Ile Ala Trp Leu Val Lys Gly Arg-NH₂
            20                  25                  30

Fig 4

EXENDIN AGONIST COMPOUNDS

RELATED APPLICATIONS

This application is a divisional of U.S. application Ser. No. 11/511,738 filed Aug. 28, 2006, which is a divisional of U.S. application Ser. No. 10/181,102 filed Jan. 27, 2003, issued as U.S. Pat. No. 7,157,555, which is a §371 of PCT/US98/16387 filed Aug. 6, 1998, which claims priority to U.S. Application No. 60/055,404 filed Aug. 8, 1997, the contents of which are hereby incorporated by reference in their entirety.

FIELD OF THE INVENTION

The present invention relates to novel compounds which have activity as exendin agonists. These compounds are useful in treatment of Type I and II diabetes, in treatment of disorders which would be benefited by agents which lower plasma glucose levels and in treatment of disorders which would be benefited with agents useful in delaying and/or slowing gastric emptying.

BACKGROUND

The following description includes information that may be useful in understanding the present invention. It is not an admission that any of the information provided herein is prior art to the presently claimed invention, nor that any of the publications specifically or implicitly referenced are prior art to that invention.

The exendins are peptides that are found in the venom of the Gila-monster, a lizard common in Arizona and Northern Mexico. Exendin-3 (SEQ ID NO:1) is present in the venom of Heloderma horridum, and exendin-4 (SEQ ID NO:2) is present in the venom of Heloderma suspectum (Eng et al, J Biol Chem, 265:20259-62, 1990; Eng et al., J Biol Chem, 267:7402-05, 1992). The amino acid sequence of exendin-3 is shown in FIG. 2. The amino acid sequence of exendin-4 is shown in FIG. 3. The exendins have some sequence similarity to several members of the glucagon-like peptide family, with the highest homology, 53%, being to GLP-1(7 36)NH$_2$ (SEQ ID NO:3) (Goke et al, J Biol Chem, 268:19650-55, 1993). GLP-1(7 36)NH$_2$, also known as proglucagon(78-107) or simply, "GLP-1," has an insulinotropic effect, stimulating insulin secretion from pancreatic β-cells. The amino acid sequence of GLP-1 is shown in FIG. 4. GLP-1 also inhibits glucagon secretion from pancreatic α-cells (Orsov et al, Diabetes, 42:658-61, 1993; D'Alessio et al, J Clin Invest, 97:133-38, 1996). GLP-1 is reported to inhibit gastric emptying (Willms et al, J Clin Endocrinol Metab 81(1): 327-32, 1996; Wettergren et al, Dig Dis Sci 38 (4):665-73, 1993), and gastric acid secretion. Schjoldager et al, Dig Dis Sci 34(5):703-8, 1989; O'Halloran et al, J Endocrinol 126(1):169-73, 1990; Wettergren et al, Dig Dis Sci 38(4):665-73, 1993). GLP-1(7 37), which has an additional glycine residue at its carboxy terminus, also stimulates insulin secretion in humans et al., Diabetes, 42:658-61, 1993). A transmembrane G-protein adenylate-cyclase-coupled receptor believed to be responsible for the insulinotropic effect of GLP-1 has been cloned from a line (Thorens, Proc. Natl. Acad. Sci. USA 89:8641-45 (1992)).

Exendin-4 reportedly acts at GLP-1 receptors on insulin-secreting cells, at dispersed acinar cells from guinea μg pancreas, and at parietal cells from stomach; the peptide is also said to stimulate somatostatin release and inhibit gastrin release in isolated stomachs (Goke, et al., Them. 268:19650-55, 1993; Schepp, et al., Eur. J. Pharmacol., 1994). Exendin-3 and exendin-4 were reportedly found to stimulate cAMP production in, and amylase release from, pancreatic acinar cells (Malhotra, R., et al., Regulators 1992; Raufman, et al., 267: 21432-37, 1992; Singh, et al., 53:47-59, 1994). Based on their insulinotropic activities, the use of exendin-3 and exendin-4 for the treatment of diabetes mellitus and the prevention of hyperglycemia has been proposed (Eng, U.S. Pat. No. 5,424, 286).

Agents which serve to delay gastric emptying have found a place in medicine as diagnostic aids in gastro-intestinal radiologic examinations. For example, glucagon is a polypeptide hormone which is produced by the a cells of the pancreatic islets of Langerhans. It is a hyperglycemic agent which mobilizes glucose by activating hepatic glycogenolysis.

It can to a lesser extent stimulate the secretion of pancreatic insulin. Glucagon is used in the treatment of insulin-induced hypoglycemia, for example, when administration of glucose intravenously is not possible.

However, as glucagon reduces the motility of the gastro-intestinal tract it is also used as a diagnostic aid in gastro-intestinal radiological examinations. Glucagon has also been used in several studies to treat various painful gastro-intestinal disorders associated with spasm. Daniel, et al. Med. J., 3:720, 1974) reported quicker symptomatic relief of acute diverticulitis in patients treated with glucagon compared with those who had been treated with analgesics or antispasmodics. A review by Glauser, et al., (J. Am. Coll. Emergency Physns, 8:228, 1979) described relief of acute esophageal food obstruction following glucagon therapy. In another study glucagon significantly relieved pain and tenderness in 21 patients with biliary tract disease compared with 22 patients treated with placebo (M. J. Stower, et al., J. Surg., 69:591-2, 1982).

Methods for regulating gastrointestinal motility using amylin agonists are described in International Application No. PCT/US94/10225, published Mar. 16, 1995. Methods for regulating gastrointestinal motility using exendin agonists are described in a U.S. Pat. No. 6,858,576. Certain exendin agonists are described in U.S. Pat. Nos. 7,223,725 and 7,220, 721.

SUMMARY OF THE INVENTION

According to one aspect, the present invention provides novel exendin agonist compounds which exhibit advantageous properties which include effects in slowing gastric emptying and lowering plasma glucose levels.

According to the present invention, provided are compounds of the formula (I) (SEQ ID NO:4):

```
Xaa₁ Xaa₂ Xaa₃ Gly Thr Xaa₄ Xaa₅ Xaa₆ Xaa₇ Xaa₈

Ser Lys Gln Xaa₉ Glu Glu Glu Ala Val Arg Leu

Xaa₁₀ Xaa₁₁ Xaa₁₂ Xaa₁₃ Leu Lys Asn Gly Gly Xaa₁₄

Ser Ser Gly Ala Xaa₁₅ Xaa₁₆ Xaa₁₇ Xaa₁₈-Z
``` wherein is $Xaa_1$ His, Arg or Tyr; $Xaa_2$ is Ser, Gly, Ala or Thr; $Xaa_3$ is Asp or Glu; $Xaa_4$ is Phe, Tyr or naphthylalanine; $Xaa_5$ is Thr or Ser; $Xaa_6$ is Ser or Thr; $Xaa_7$ is Asp or Glu; $Xaa_s$ is Leu, Ile, Val, pentylglycine or Met; $Xaa_9$ is Leu, Ile, pentylglycine, Val or Met; $Xaa_{10}$ is Phe, Tyr or naphthylalanine; $Xaa_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $Xaa_{14}$, $Xaa_{15}$, $Xaa_{16}$ and $Xaa_{r7}$ are independently Pro, homoproline, 3Hyp, 4Hyp, thioproline, N-alkylglycine, N-alkylpentylglycine or N-alkylalanine; Xaa$_{18}$ is Ser, Thr or Tyr; and Z is —OH or —NH$_2$; with the proviso that the compound does not have the formula of either SEQ ID. NO:1 or 2. Also included within the scope of the present invention are pharmaceutically acceptable salts of the compounds of formula (I) and pharmaceutical compositions including said compounds and salts thereof.

Also provided are compounds of the formula II (SEQ ID NO:36):

Xaa$_1$ Xaa$_2$ Xaa$_3$ Gly Thr Xaa$_4$ Xaa$_5$ Xaa$_6$ Xaa$_7$ Xaa$_8$ Ser

Lys Gln Xaa$_9$ Glu Glu Glu Ala Val Arg Leu Xaa$_{10}$

Xaa$_{11}$ Xaa$_{12}$ Xaa$_{13}$ Leu X$_1$ Gly Gly Xaa$_{14}$ Ser Ser Gly

Ala Xaa$_{15}$ Xaa$_{16}$ Xaa$_{17}$ Xaa$_{18}$-Z wherein Xaa$_1$ is His, Arg, Tyr or 4-imidazopropionyl; Xaa$_2$ is Ser, Gly, Ala or Thr; Xaa$_3$ is Asp or Glu; Xaa$_4$ is Phe, Tyr or naphthylalanine; Xaa$_5$ is Thr or Ser; Xaa$_6$ is Ser or Thr; Xaa$_7$ is Asp or Glu; Xaa$_8$ is Leu, Ile, Val, pentylglycine or Met; Xaa$_9$ is Leu, Ile, pentylglycine, Val or Met; Xaa$_{10}$ is Phe, Tyr or naphthylalanine; Xaa$_{11}$ is Ile, Val, Leu, pentylglycine, tert-butylglycine or Met; Xaa$_{12}$ is Glu or Asp; Xaa$_{13}$ is Trp, Phe, Tyr, or naphthylalanine; X$_1$ is Lys Asn, Asn Lys, Lys-NH$^e$-R Asn, Asn Lys-NH$^e$-R where R is Lys, Arg, straight chain or branched alkanoyl or cycloalkylalkanoyl; Xaa$_{14}$, Xaa$_{15}$, Xaa$_{16}$ and Xaa$_{17}$ are independently Pro, homoproline, 3Hyp, 4Hyp, thioproline, N-alkylglycine, N-alkylpentylglycine or N-alkylalanine; Xaa$_{18}$ is Ser, Thr or Tyr; and Z is —OH or —NH$_2$; with the proviso that the compound does not have the formula of either SEQ ID NO:1 or 2. Also included within the scope of the present invention are pharmaceutically acceptable slats of the compounds of formula and pharmaceutical compositions including said compounds and salts thereof.

Definitions: In accordance with the present invention and as used herein, the following terms are defined to have the following meanings, unless explicitly stated otherwise. The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine glutamic acid (Glu), glycine histidine isoleucine (Ile), leucine Lysine (Lys), methionine (Met), phenylalanine (Phe), proline (Pro), serine (Ser), threonine (Thr), typtophan (Trp), tyrosine (Tyr) and valine Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically codified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is an amino acid side chain, typically H or a carbon containing substitutent; or (2)

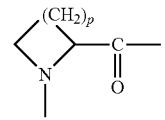

wherein p is 1, 2 or 3 representing the azetidinecarboxylic acid, proline or pipecolic acid residues, respectively.

The term "lower" referred to herein in connection with organic radicals such as alkyl groups defines such groups with up to and including about 6, preferably up to and including 4 and advantageously one or two carbon atoms. Such groups may be straight chain or branched chain.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

In addition, the following abbreviations stand for the following: "ACN" or "CH$_3$CN" refers to acetonitrile. "Boc", "tBoc" or Tboc" refers to t-butoxy carbonyl. "DCC" refers to N,N'-dicyclohexylcarbodiimide. "Fmoc" refers to fluorenyl-methoxycarbonyl. "HBTU" refers to 2-(1H-benzotriazol-1-yl)-1,1,3,3-tetramethyluronium hexafluorophosphate. "HOBt" refers to 1-hydroxybenzotriazole monohydrate. "homoP" or "hPro" refers to homoproline. "MeAla" or "Nme" refers to N-methylalanine. "naph" refers to naphthylalanine. "pG" or pGly" refers to pentylglycine. "tBuG" refers to tertiary-butylglycine. "ThioP" or tPro" refers to thioproline.

BRIEF DESCRIPTION OF THE DRAWINGS

FIG. 1 depicts the amino acid sequences for certain compounds of the present invention (SEQ ID NOs: 5 to 35).

FIG. 2 depicts the amino acid sequence for exendin-3 (SEQ ID NO: 1).

FIG. 3 depicts the amino acid sequence for exendin-4 (SEQ ID NO: 2).

FIG. 4 depicts the amino acid sequence for GLP-1 (SEQ ID NO: 3).

DETAILED DESCRIPTION OF THE INVENTION

Figure 5:
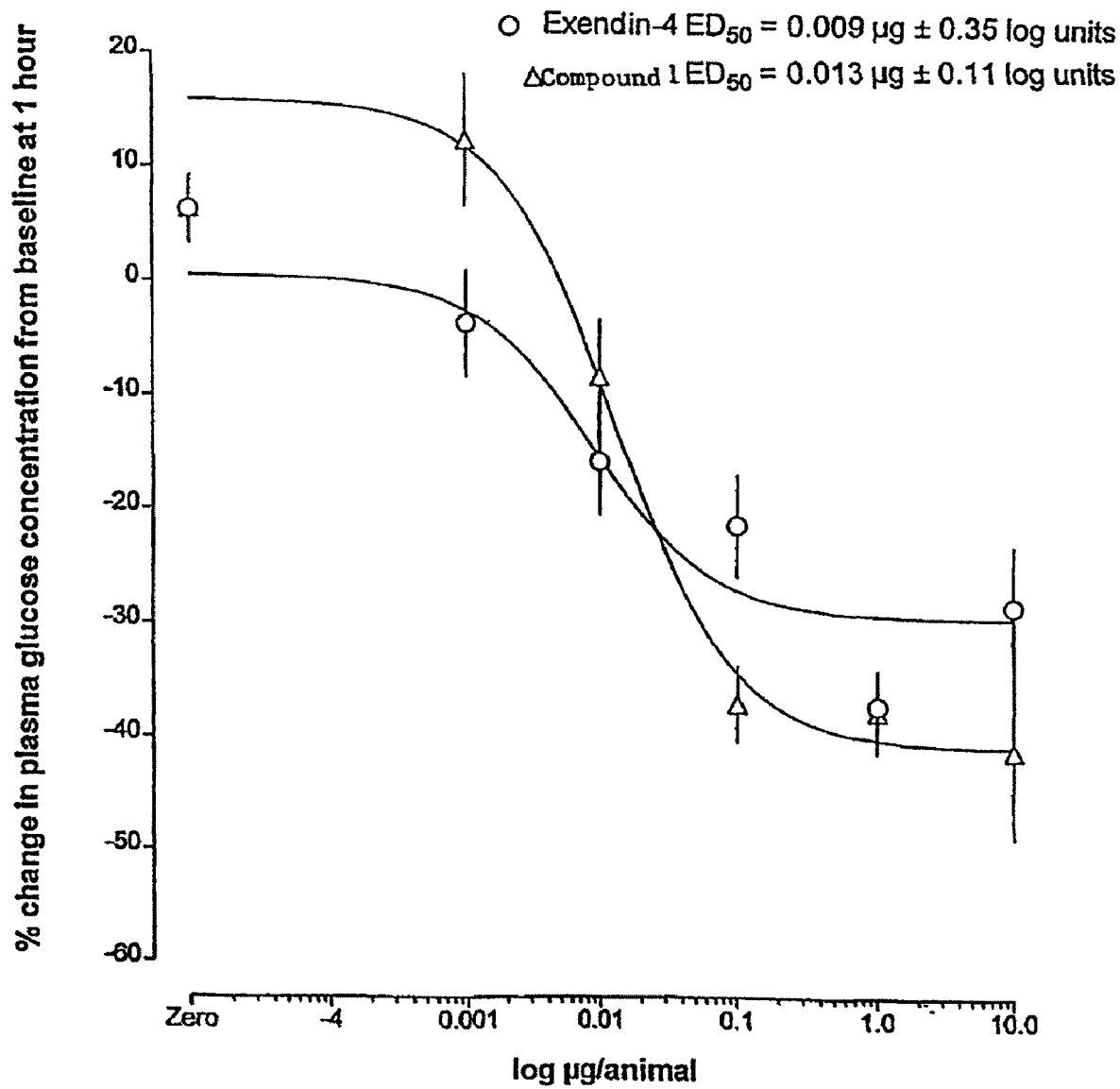
FIG. 5 depicts dose dependent effects of exendin-4 in comparison with compound 1 of FIG. 1 [SEQ: ID: NO: 5] on plasma glucose levels in db/db mice.

According to the present invention, provided are compounds of the formula (I) (SEQ ID NO:4):

Xaa$_1$ Xaa$_2$ Xaa$_3$ Gly Thr Xaa$_4$ Xaa$_5$ Xaa$_6$ Xaa$_7$ Xaa$_8$ Ser

Lys Gln Xaa$_9$ Glu Glu Glu Ala Val Arg Leu Xaa$_{10}$

Xaa$_{11}$ Xaa$_{12}$ Xaa$_{13}$ Leu Lys Asn Gly Gly Xaa$_{14}$ Ser

Ser Gly Ala Xaa$_{15}$ Xaa$_{16}$ Xaa$_{17}$ Xaa$_{18}$-Z wherein is Xaa$_1$ His, Arg or Tyr; Xaa$_2$ is Ser, Gly, Ala or Thr; Xaa$_3$ is Asp or Glu; Xaa$_4$ is Phe, Tyr or naphthylalanine; Xaa$_5$ is Thr or Ser; Xaa$_6$ is Ser or Thr; Xaa$_7$ is Asp or Glu; Xaa$_8$ is Leu, Ile, Val, pentylglycine or Met; Xaa$_9$ is Leu, Ile, pentylglycine, Val or Met; Xaa$_{10}$ is Phe, Tyr or naphthylalanine; Xaa$_{11}$ is Ile, Val, Leu, pentylglycine, tert-butylglycine or Met; Xaa$_{12}$ is Glu or Asp; Xaa$_{13}$ is Trp, Phe, Tyr, or naphthylalanine; Xaa$_{14}$, Xaa$_{15}$, Xaa$_{16}$ and Xaa$_{17}$ are independently Pro, homoproline, 3Hyp, 4Hyp, thioproline, N-alkylglycine, N-alkylpentylglycine or N-alkylalanine; Xaa$_{18}$ is Ser, Thr or Tyr; and Z is —OH or —NH$_2$; with the proviso that the compound does not have the formula of either SEQ ID. NO:1 or 2. Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds of formula (I) include those having amino acid sequences of SEQ ID NOs:5 to 35.

Preferred exendin agonist compounds of formula (I) include those wherein Xaa$_1$ is His or Tyr. More preferably Xaa$_1$ is His. Preferred are those such compounds wherein Xaa$_2$ is Gly. Preferred are those such compounds wherein Xaa$_9$ is Leu, pentylglycine or Met. Preferred compounds of formula (I) include those wherein Xaa$_{13}$ is Trp or Phe. Also preferred are compounds of formula (I) wherein Xaa$_4$ is Phe or naphthylalanine; Xaa$_{11}$ is Ile or Val and Xaa$_{14}$, Xaa$_{15}$, Xaa$_{16}$ and Xaa$_{17}$ are independently selected from Pro, homoproline, thioproline or N-alkylalanine. Preferably N-alkylalanine has a N-alkyl group of 1 to about 6 carbon atoms. According to an especially preferred aspect, Xaa$_{15}$, Xaa$_{16}$ and Xaa$_{17}$ are the same amino acid residue. Preferred are compounds of formula (I) wherein Xaa$_{18}$ is Ser or Tyr, more preferably Ser. Preferably Z is —NH$_2$.

According to one aspect, preferred are compounds of formula (I) wherein Xaa$_1$ is His or Tyr, more preferably His; Xaa$_2$ is Gly; Xaa$_4$ is Phe or naphthylalanine; Xaa$_9$ is Leu, pentylglycine or Met; Xaa$_{10}$ is Phe or naphthylalanine; Xaa$_{11}$ is Ile or Val; Xaa$_{14}$, Xaa$_{15}$, Xaa$_{16}$ and Xaa$_{17}$ are independently selected from Pro, homoproline, thioproline or N-alkylalanine; and Xaa$_{18}$ is Ser or Tyr, more preferably Ser. More preferably Z is —NH$_2$.

According to an especially preferred aspect, especially preferred compounds include those of formula (I) wherein: Xaa$_1$ is His or Arg; Xaa$_2$ is Gly; Xaa$_3$ is Asp or Glu; Xaa$_4$ is Phe or napthylalanine; Xaa$_5$ is Thr or Ser; Xaa$_6$ is Ser or Thr; Xaa$_7$ is Asp or Glu; Xaa$_8$ is Leu or pentylglycine; Xaa$_9$ is Leu or pentylglycine; Xaa$_{10}$ is Phe or naphthylalanine; Xaa$_{11}$ is Ile, Val or t-butyltylglycine; Xaa$_{12}$ is Glu or Asp; Xaa$_{13}$ is Trp or Phe; Xaa$_{14}$, Xaa$_{15}$, Xaa$_{16}$ and Xaa$_{17}$ are independently Pro, homoproline, thioproline, or N-methylalanine; Xaa$_{18}$ is Ser or Tyr: and Z is OH or NH$_2$; with the proviso that the compound does not have the formula of either SEQ ID NO:1 or 2. More preferably Z is —NH$_2$. Especially preferred compounds of formula (I) include those having the amino acid sequence of SEQ ID NOs:5, 6, 17, 18, 19, 22, 24, 31, 32 and 35.

According to an especially preferred aspect, provided are compounds of formula (I) where Xaa$_9$ is Leu, Ile, Val or pentylglycine, more preferably Leu or pentylglycine, and Xaa$_{13}$ is Phe, Tyr or naphthylalanine, more preferably Phe or naphthylalanine. These compounds will exhibit advantageous duration of action and be less subject to oxidative degration, both in vitro and in as well as during synthesis of the compound.

Also provided are compounds of the formula II (SEQ ID NO:36):

Xaa$_1$ Xaa$_2$ Xaa$_3$ Gly Thr Xaa$_4$ Xaa$_5$ Xaa$_6$ Xaa$_7$ Xaa$_8$ Ser

Lys Gln Xaa$_9$ Glu Glu Glu Ala Val Arg Leu Xaa$_{10}$

Xaa$_{11}$ Xaa$_{12}$ Xaa$_{13}$ Leu X$_1$ Gly Gly Xaa$_{14}$ Ser Ser Gly

Ala Xaa$_{15}$ Xaa$_{16}$ Xaa$_{17}$ Xaa$_{18}$-Z wherein is Xaa$_1$ His, Arg, Tyr or 4-imidazopropionyl; Xaa$_2$ is Ser, Gly, Ala or Thr; Xaa$_3$ is Asp or Glu; Xaa$_4$ is Phe, Tyr or naphthylalanine; Xaa$_5$ is Thr or Ser; Xaa$_6$ is Ser or Thr; Xaa$_7$ is Asp or Glu; Xaa$_8$ is Leu, Ile, Val, pentylglycine or Met; Xaa$_9$ is Leu, Ile, pentylglycine, Val or Met; Xaa$_{10}$ is Phe, Tyr or naphthylalanine; Xaa$_{11}$ is Ile, Val, Leu, pentylglycine, tert-butylglycine or Met; Xaa$_{12}$ is Glu or Asp; Xaa$_{13}$ is Trp, Phe, Tyr, or naphthylalanine; X$_1$ is Lys Asn, Asn Lys, Lys-NH$^e$-R Asn, or Asn Lys-NH$^e$-R where R is Lys, Arg, C$_1$-C$_{10}$ straight chain or branched alkanoyl or cycloalkyanoyl; Xaa$_{14}$, Xaa$_{15}$, Xaa$_{16}$ and Xaa$_{17}$ are independently Pro, homoproline, 3Hyp, 4Hyp, thioproline, N-alkylglycine, N-alkylpentylglycine or N-alkylalanine; Xaa$_{18}$ is Ser, Thr or Tyr; and Z is —OH or —NH$_2$; with the proviso that the compound does not have the formula of either SEQ ID. NO:1 or 2. Also included within the scope of the present invention are pharmaceutically acceptable slats of the compounds of formula (II) and pharmaceutical compositions including said compounds and salts thereof. Suitable compounds of formula (II) include that compound having the amino acid sequences of SEQ ID NOs:37-40.

Preferred exendin agonist compounds of formula include those wherein Xaa$_1$ is His, Tyr or 4-imidazopropionyl. More preferably, Xaa$_1$ is His or 4-imidazopionyl. Preferred are those compounds of formula (II) wherein Xaa$_2$ is Gly. Preferred are those compounds of formula (II) wherein Xaa$_9$ is Leu, pentylglycine or Met. Preferred are those compounds of formula (II) wherein Xaa$_{13}$ is Trp or Phe. Preferred are those compounds of formula (II) wherein X$_1$ is Lys Asn, or Lys-NH$^e$-R Asn, where R is Lys, Arg, C$_1$-C$_{10}$ straight chain or branched alkanoyl.

Also preferred are compounds of formula (II) wherein Xaa$_4$ is Phe or naphthylalanine; Xaa$_{10}$ is Phe or naphthylalanine; Xaa$_{11}$ is Ile or Val and Xaa$_{14}$, Xaa$_{15}$, Xaa$_{16}$ and Xaa$_{17}$ are independently selected from Pro, homoproline, thioproline or N-alkylalanine. According to an especially preferred aspect, Xaa$_{18}$ is Ser or Tyr. Preferred are those such compounds wherein Xaa$_{18}$ is Ser. Preferably, Z is —NH$_2$.

According to one preferred aspect, preferred are compounds of formula (II) wherein Xaa$_4$ is Phe or naphthylalanine; Xaa$_{10}$ is Phe or naphthylalanine; Xaa$_{11}$ is Ile or Val, X$_1$ is Lys Asn, or Lys-NH$^e$-R Asn, where R is Lys, Arg, C$_1$-C$_{10}$ straight chain or branched alkanoyl and Xaa$_{14}$, Xaa$_{15}$, Xaa$_{16}$ and Xaa$_{17}$ are independently selected from Pro, homoproline, thioproline or N-alkylalanine.

The compounds referenced above form salts with various inorganic and organic acids and bases. Such salts include salts prepared with organic and inorganic acids, for example, HCl, HBr, H2SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Utility the compounds described above are useful in view of their pharmacological properties. In particular, the compounds of the invention are exendin agonists, and possess activity as agents to regulate gastric motility and to slow gastric emptying, as evidenced by the ability to reduce postprandial glucose levels in mammals.

Preparation of Compounds: the Compounds of the Present Invention May be Prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Inc. (Foster City, Calif.). The following side-chain protected amino acids may be purchased from Applied Inc.: Arg(Mts), Fmoc-Arg(Pmc), Boc-Thr(Bzl), Fmoc-Thr(t-Bu), Ser(Bzl), Fmoc-Ser(t-Bu), Boc-Tyr(BrZ), Fmoc-Tyr(t-Bu), Lys(Cl—Z), Fmoc-Lys(Boc), Boc-Glu (Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Inc., Foster City, Calif.) using the NMP/HOBt (Option 1) system and tBoc or Fmoc chemistry (see, Applied Users Manual for the 430A Peptide Synthesizer, Version 1.3B Jul. 1, 1988, section 6, pp. 49-70, Applied Inc., Foster City, Calif.) with capping. Boc-peptide-resins may be cleaved with HF to 1 hour). The peptide may be extracted from the resin with alternating water and acetic acid, and the filtrates lyophilized. The Fmoc-peptide resins may be cleaved according to standard methods (Introduction to Cleavage Techniques, Applied Inc., 1990, pp. 6-12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10 2.2×25 cm; Vydac, Hesperia, Calif.) may be used to isolate peptides, and purity may be determined using a C4, C8 or C18 analytical column (5 μ, 0.46×25 cm; Vydac). Solvents (A=0.1% TFA/water and TFA/CH$_3$CN) may be delivered to the analytical column at a flow-rate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis 20-24 h). Hydrolysates may be derivatized and analyzed by standard methods (Cohen, et Method: A Manual of Advanced Techniques for Amino Acid Analysis, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied 20 mass spectrometer. Electrospray mass spectroscopy may be carried and on a VG-Trio machine.

Peptide compounds useful in the invention may also be prepared using recombinant DNA techniques, using methods now known in the art. See, Sambrook Molecular Cloning: A Laboratory Manual, 2d Ed., Cold Spring Harbor (1989). Non-peptide compounds useful in the present invention may be prepared by art-known methods.

The compounds referenced above may form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, sodium and potassium salts, and alkali earth salts, calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed or by freeze-drying or by exchanging the ions of an existing salt for another ion on a suitable ion exchange resin.

Formulation and Administration: Compounds of the invention are useful in view of their exendin-like effects, and may conveniently be provided in the form of formulations suitable for parenteral (including intravenous, intramuscular and subcutaneous) or nasal or oral administration. In some cases, it will be convenient to provide an exendin or exendin agonist and another anti-gastric-emptying agent, such as glucagon, an amylin, or an amylin agonist, in a single composition or solution for administration together. In other cases, it may be more advantageous to administer another anti-emptying agent separately from said exendin or exendin agonist. In yet other cases, it may be beneficial to provide an exendin or an exendin agonist either co-formulated or separately with other glucose lowering agents such as insulin. A suitable administration format may best be determined by a medical practitioner for each patient individually. Suitable pharmaceutically acceptable carriers and their formulation are described in standard formulation treatises, Wang, Y. J. and Hanson, M. A. "Parenteral Formulations of Proteins and Peptides: Stability and Stabilizers," Supp. 42:2 S (1988).

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The claimed compounds can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethane-sulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compounds will be provided in dosage unit form containing an amount of an exendin agonist, with or without another anti-emptying agent. Therapeutically effective amounts of an exendin agonist for use in the control of gastric emptying and in conditions in which gastric emptying is beneficially slowed or regulated are those that decrease post-prandial blood glucose levels, preferably to no more than about 8 or 9 mM or such that blood glucose levels are reduced as desired. In diabetic or glucose intolerant individuals, plasma glucose levels are higher than in normal individuals. In such individuals, beneficial reduction or "smoothing" of post-prandial blood glucose levels, may be obtained. As will be recognized by those in the field, an effective amount of therapeutic agent will vary with many factors including the age and weight of the patient, the patient's physical condition, the blood sugar level or level of inhibition of gastric emptying to be obtained, and other factors.

Such pharmaceutical compositions are useful in causing gastric hypomotility in a subject and may be used as well in other disorders where gastric motility is beneficially reduced.

The effective daily anti-emptying dose of the compounds will typically be in the range of 0.01 or 0.03 to about 5 mg/day, preferably about 0.01 or 0.5 to 2 mg/day and more preferably about 0.01 or 0.1 to 1 mg/day, for a 70 kg patient, administered in a single or divided doses. The exact dose to be administered is determined by the attending clinician and is dependent upon where the particular compound lies within the above quoted range, as well as upon the age, weight and condition of the individual. Administration should begin at the first sign of symptoms or shortly after diagnosis of diabetes mellitus. Administration may be by injection, preferably subcutaneous or intramuscular. Orally active compounds may be taken orally, however dosages should be increased 5-10 fold.

Generally, in treating or preventing elevated, inappropriate, or undesired post-prandial blood glucose levels, the compounds of this invention may be administered to patients in need of such treatment in a dosage ranges similar to those given above, however, the compounds are administered more frequently, for example, one, two, or three times a day.

The optimal formulation and mode of administration of compounds of the present application to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

To assist in understanding the present invention the following Examples are included which describe the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Preparation of Amidated Peptide Having SEQ ID NO:5

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied In general, single-coupling cycles were used throughout the synthesis and Fast Moc (HBTU activation) chemistry was employed. However, at some positions coupling was less efficient than expected and double couplings were required. In particular, residues $Asp_9$, $Thr_7$ and $Phe_6$ all required double coupling. Deprotection (Fmoc group removal) of the growing peptide chain using piperidine was not always efficient. Double deprotection was required at positions $Arg_{20}$, $Val_{19}$ and $Leu_{14}$. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Inc.). The peptide was precipitated in ether/water (50 mL) and centrifuged. The precipitate was reconstituted in glacial acetic acid and lyophilized. The lyophilized peptide was dissolved in water). Crude purity was about 55%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 60% Solvent B in Solvent A over 30 minutes) of the lyophilized peptide gave product peptide having an observed retention time of 14.5 minutes. Electrospray Mass Spectrometry (M): calculated 4131.7; found 4129.3.

EXAMPLE 2

Preparation of Peptide Having SEQ ID NO:6

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis were Solvent A (0.1% TFA in water) and Solvent B (0.1% TFA in ACN). Analytical RP-HPLC (gradient 25% to 75% Solvent B in Solvent A over 30 minutes) of the lyophilized peptide gave product peptide having an observed retention time of 21.5 minutes. Electrospray Mass Spectrometry (M): calculated 4168.6; found 4171.2.

EXAMPLE 3

Preparation of Peptide Having SEQ ID NO:7

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis were Solvent A (0.1% TFA in water) and Solvent B (0.1% TFA in ACN). Analytical RP-HPLC (gradient 30% to 60% Solvent B in Solvent A over 30 minutes) of the lyophilized peptide gave product peptide having an observed retention time of 17.9 minutes. Electrospray Mass Spectrometry (M): calculated 4147.6; found 4150.2.

EXAMPLE 4

Preparation of Peptide Having SEQ ID NO:8

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis were Solvent A (0.1% TFA in water) and Solvent B (0.1% TFA in ACN). Analytical RP-HPLC (gradient 35% to 65% Solvent B in Solvent A over 30 minutes) of the lyophilized peptide gave product peptide having an observed retention time of 19.7 minutes. Electrospray Mass Spectrometry (M): calculated 4212.6; found 4213.2.

EXAMPLE 5

Preparation of Peptide Having SEQ ID NO:9

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis were Solvent A (0.1% TFA in water) and Solvent B (0.1% TFA in ACN). Analytical RP-HPLC (gradient 30% to 50% Solvent B in Solvent A over 30 minutes) of the lyophilized peptide gave product peptide having an observed retention time of 16.3 minutes. Electrospray Mass Spectrometry (M): calculated 4262.7; found 4262.4.

EXAMPLE 6

Preparation of Peptide Having SEQ ID NO:10

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6

EXAMPLE 7

Preparation of Peptide Having SEQ ID NO:11

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4224.7.

EXAMPLE 8

Preparation of Peptide Having SEQ ID NO:12

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6.

EXAMPLE 9

Preparation of Peptide Having SEQ ID NO:13

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4186.6.

EXAMPLE 10

Preparation of Peptide Having SEQ ID NO:14

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4200.7.

EXAMPLE 11

Preparation of Peptide Having SEQ ID NO:15

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4200.7.

EXAMPLE 12

Preparation of Peptide Having SEQ ID NO:16

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4202.7.

EXAMPLE 13

Preparation of Peptide Having SEQ ID NO:17

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 14

Preparation of Peptide Having SEQ ID NO:18

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4184.6.

EXAMPLE 15

Preparation of Peptide Having SEQ ID NO:19

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 16

Preparation of Peptide Having SEQ ID NO:20

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4224.7.

EXAMPLE 17

Preparation of Peptide Having SEQ ID NO:21

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6.

EXAMPLE 18

Preparation of Peptide Having SEQ ID NO:22

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4115.5.

EXAMPLE 19

Preparation of Peptide Having SEQ ID NO:23

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4188.6.

EXAMPLE 20

Preparation of Peptide Having SEQ ID NO:24

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4131.6.

EXAMPLE 21

Preparation of Peptide Having SEQ ID NO:25

The above-identified peptide is assembled on 4-(2'-4'-aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4172.6.

EXAMPLE 22

Preparation of Peptide Having SEQ ID NO:26

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4145.6.

EXAMPLE 23

Preparation of Peptide Having SEQ ID NO:27

The above-identified peptide is assembled on 4-(2'-4'-aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the thioproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4266.8.

EXAMPLE 24

Preparation of Peptide Having SEQ ID NO:28

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the thioproline positions 38, 37 and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4246.8.

EXAMPLE 25

Preparation of Peptide Having SEQ ID NO:29

The above-identified peptide is assembled on 4-(2'-4'-aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the homoproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4250.8.

EXAMPLE 26

Preparation of Peptide Having SEQ ID NO:30

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the homoproline positions 38, 37, and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4234.8.

EXAMPLE 27

Preparation of Peptide Having SEQ ID NO:31

The above-identified peptide is assembled on 4-(2'-4'-aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the thioproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4209.8.

EXAMPLE 28

Preparation of Peptide Having SEQ ID NO:32

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the homoproline positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4193.7.

EXAMPLE 29

Preparation of Peptide Having SEQ ID NO:33

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the N-methylalanine positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3858.2.

EXAMPLE 30

Preparation of Peptide Having SEQ ID NO:34

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the N-methylalanine positions 38, 37 and 36. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3940.3.

EXAMPLE 31

Preparation of Peptide Having SEQ ID NO:35

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the N-methylalanine positions 38, 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3801.1.

EXAMPLE 32

Preparation of Peptide Having SEQ ID NO:36

4-Imidazolylpropionyl-Gly Glu Gly Thr Phe Thr Ser Asp Leu Ser Lys Gln Met Glu Glu Glu Ala Val Arg Leu Phe Ile Glu Trp Leu Asn Gly Gly Pro Ser Ser Gly Ala Pro Pro Pro Ser-NH$_2$ (SEQ ID NO:36) is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the proline positions 38, 37, 36 and 31. acid is used for coupling at position 27. Instead of using protected His for the final coupling at position 1,4-imidazolylpropionic acid is coupled directly to the N-terminus of residues 2-39 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated.

EXAMPLE 33

Preparation of Peptide Having SEQ ID NO:37

4-Imidazolylpropionyl-Gly Glu Gly Thr Phe Thr Ser Asp Leu Ser Lys Gln Leu Glu Glu Glu Ala Val Arg Leu Phe Ile Glu Phe Leu Asn Gly Gly Pro Ser Ser Gly Ala Pro Pro Pro Ser-NH$_2$ (SEQ ID NO:37) is assembled on dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the proline positions 38, 37, 36 and 31. acid is used for coupling at position 27. Instead of using protected His for the final coupling at position 1,4-imidazolylpropionic acid is coupled directly to the N-terminus of residues 2-39 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated.

EXAMPLE 34

Preparation of Peptide Having SEQ ID NO:38

4-Imidazolylpropionyl-Gly Glu Gly Thr Phe Thr Ser Asp Leu Ser Lys Gln Met Glu Glu Glu Ala Val Arg Leu Phe Ile Glu Trp Leu Asn Gly Gly Pro Ser Ser Gly Ala Pro Pro Pro Ser-NH$_2$ (SEQ ID NO:38) is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the proline positions 38, 37, 36 and 31. acid is used for coupling at position 28. Instead of using protected His for the final coupling at position 1,4-imidazolylpropionic acid is coupled directly to the N-terminus of protected residues 2-39 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4294.5.

EXAMPLE 35

Preparation of Peptide Having SEQ ID NO:39

4-Imidazolylpropionyl-Gly Glu Gly Thr Phe Thr Ser Asp Leu Ser Lys Gln Leu Glu Glu Glu Ala Val Arg Leu Phe Ile Glu Phe Leu Asn Gly Gly Pro Ser Ser Gly Ala Pro Pro Pro Ser-NH$_2$ (SEQ ID NO:39) is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Inc.), cleaved from the resin, deprotected and purified in a similar way to Example 1. Additional double couplings are required at the proline positions 38, 37, 36 and 31. acid is used for coupling at position 28. Instead of using protected His for the final coupling at position 1,4-imidazolylpropionic acid is coupled directly to the N-terminus of residues 2-39 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4242.7.

EXAMPLE 36

Preparation of C-terminal Carboxylic Acid to the Above C-terminal Sequences: The above peptides of Examples 1 to 35 are assembled on the so called Wang resin (p-alkoxybenzylalcohol resin (Bachem, 0.54 mmole/g)) using Fmoc-protected amino acids (Applied Inc.), cleaved from the resin, deprotected and purified in a similar way to Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLES A to D

Reagents Used: GLP-1 was purchased from Bachem (Torrance, Calif.), all other peptides were prepared in house using synthesis methods such as those described therein. All chemicals were of the highest commercial grade. The cAMP SPA immunoassay was purchased from Amersham. The radioligands were purchased from New England Nuclear (Boston, RINm5f cells (American Type Tissue Collection, Rockville, Md.) were grown in DME/F12 medium containing 10% fetal bovine serum and 2 mM L-glutamine. Cells were grown at 37° C. and 5% humidified air and medium was replaced every 2 to 3 days. Cells were grown to confluence then harvested and homogenized using on a Polytron homogenizer. Cell homogenates were stored frozen at −70° C. until used.

Example A

GLP-1 Receptor Binding Studies

GLP-1 Receptor Receptor binding was assessed by measuring displacement of [$^{125}$I] human GLP-1 (7-36) or [$^{125}$I] Exendin (9-39) from RINm5f membranes. Assay buffer contained 5 bestatin 1 phosphoramidon, 1 mg/ml bovine serum albumin (fraction V), 1 mg/ml bacitracin, and 1 mM MgC12 in 20 mM HEPES, pH 7.4. To measure binding, 30 membrane protein (Bradford protein assay) was resuspended in 200 assay buffer and incubated with 60 μM human GLP-1 or Exendin (9-39) and unlabeled peptides for 120 minutes as in 96 well plates (Nagle Nunc, Rochester, Incubations were terminated by rapid filtration with cold phosphatebuffered saline, pH 7.4, through polyethyleneimine-treated GF/B glass fiber filters (Wallac Inc., Gaithersburg, Md.) using a Tomtec Mach II plate harvester (Wallac Inc., Gaithersburg, Md.). Filters were dried, combined with scintillant, and radioactivity determined in a liquid scintillant counter (Wallac Peptide samples were run in the assay as duplicate points at 6 dilutions over a concentration range of to generate response curves. The biological activity of a sample is expressed as an value, calculated from the raw data using an iterative curve-fitting program using a 4-parameter logistic equation (Prism, GraphPAD Software).

Example B

Cyclase Activiation Study

Assay buffer contained 10 GTP, 0.75 mM ATP, 2.5 mM MgCl2, 0.5 mM phosphocreatine, 12,5 U/ml creatine kinase, 0.4 mg/ml aprotinin, 1 in 50 mM HEPES, pH 7.4. Membranes and peptides were combined in 100 ml of assay buffer in 96 well filter-bottom plates (Millipore Corp., Bedford, Mass.). After 20 minutes incubation at 37° C., the assay was terminated by transfer of supernatant by filtration into a fresh 96 well plate using a Millipore vacuum manifold. Supernatant cAMP contents were quantitated by SPA immunoassay. Peptide samples were run in the assay as triplicate points at 7 dilutions over a concentration range of to to generate response curves. The biological activity of a particular sample was expressed as an value, calculated as described above. Results are tabulated in Table I.

TABLE I

Activity in the RINm5f Cyclase Assay

| | $EC_{50}$ |
|---|---|
| Exendin-4 (SEQ ID NO: 2) | 0.23 |
| Compound 1 (SEQ ID NO: 5) | 0.17 |
| Compound 2 (SEQ ID NO: 6) | 0.23 |
| Compound 3 (SEQ ID NO: 7) | 0.42 |

Example C

Determination of Blood Glucose Levels in db/db Mice—1 Hour Protocol. C57BL/6J-m=/=Lepr$^{db}$ mice, at least 3 months of age were utilized for the study. The mice were obtained from The Jackson Laboratory and allowed to acclimate for at least one week in the vivarium. Mice were housed in groups of ten at 22°±1° C. with a 12:12 light:dark cycle, with lights on at 6 a.m.

All animals were deprived of food for 2 hours before taking baseline blood samples. Approximately 100 of blood was drawn from each mouse via eye puncture, after a light anesthesia with metophane. After collecting baseline blood samples, to measure plasma glucose concentrations, all animals receive subcutaneous injections of either vehicle, exendin-4 or test compound in concentrations indicated. Blood samples were drawn again, using the same procedure, after exactly one hour from the injections, and plasma glucose concentrations were measured.

For each animal, the % change in plasma value, from baseline value, was calculated and a dose dependent relationship was evaluated using Graphpad Prizm™ software.

FIG. 5 depicts the effects of varying doses of exendin-4 and Compound 1 of FIG. 1 (SEQ ID NO:5) on plasma glucose levels.

Example D

The following study was carried out to examine the effects of exendin-4, exendin-4 acid and an exendin agonist (Compound 1 of FIG. 1 (SEQ ID NO:5)) on gastric emptying in rats. This experiment followed a modification of the method of Scarpignato, et al., Arch. Int. Pharmacodyn. Ther., 246:286-94 (1980).

Male Harlan Sprague Dawley (HSD) rats were used. All animals were housed at 22.7±0.8° C. in a 12:12 hour light:dark cycle (experiments being performed during the light cycle) and were fed and watered ad libitum (Diet LM-485, Teklad, Madison, Wis.). Exendin-4 and exendin-4 acid were synthesized according to standard peptide synthesis methods. The preparation of Compound 1 (SEQ ID NO:5) is described in Example 1.

The determination of gastric emptying by the method described below was performed after a fast of hours to ensure that the stomach contained no chyme that would interfere with spectrophotometric absorbance measurements.

Conscious rats received by gavage, of an acaloric gel containing 1.5% methyl cellulose (M-0262, Sigma Chemical Co, St Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In separate experiments on 7 rats, the stomach and small intestine were both excised and opened into an alkaline solution. The quantity of phenol red that could be recovered from the upper gastrointestinal tract within 20 minutes of gavage was dye which appeared to bind irrecoverably to the gut luminal surface may have accounted for the balance. To account for a maximal dye recovery of less than 100%, percent of stomach contents remaining after 20 min were expressed as a fraction of the gastric contents recovered from control rats sacrificed immediately after gavage in the same experiment. Percent gastric contents remaining= (absorbance at 20 min)/(absorbance at mm)×100.

In baseline studies, with no drug treatment, gastric emptying over 20 min was determined. In dose-response studies, rats were treated with 0.01, 0.1, 0.3, 1, 10 and 100 μg of exendin-4, 0.01, 0.03, 0.1, 1, 10 and 100 μg exendin-4 acid, and 0.1, 0.3, 1, 10 and 100 μg of Compound 1 (SEQ ID NO:5).

Figure 6:
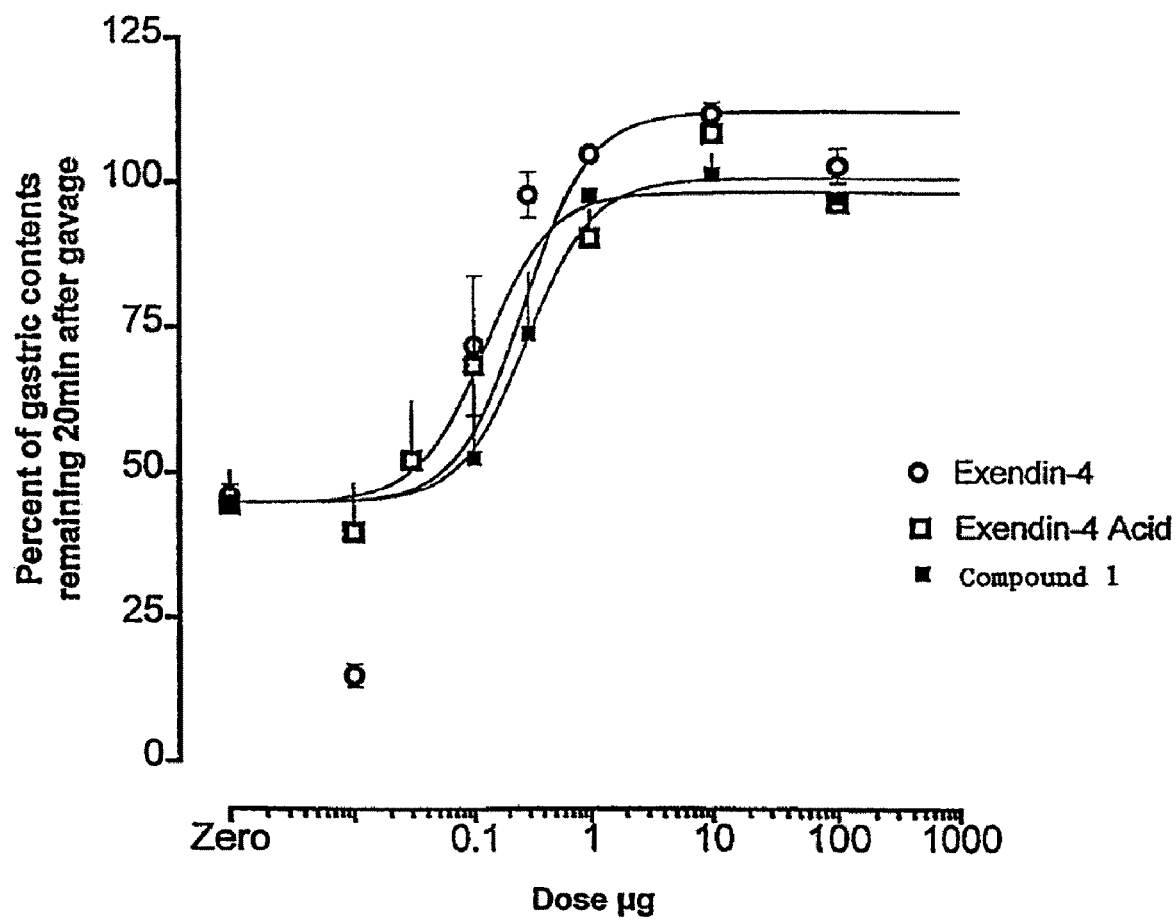
FIG. 6 depicts a comparison of effects on gastric emptying of exendin-4, exendin-4 acid and compound I of FIG. 1 [SEQ ID NO: 5].

The results are shown in FIG. 6. The results, shown in FIG. 6 and Table II, show that the exendin agonists, exendin-4 acid and compound 1 are potent inhibitors of gastric emptying. The $EC_{50}$ of exendin-4 was 0.27 μg. The $EC_{50}$ of exendin-4 acid and Compound 1 were comparable (0.12 μg and 0.29 μg, respectively).

TABLE II

| Compound | $EC_{50}$ (μg) |
|---|---|
| exendin-4 | 0.27 |
| Exendin-4 acid | 0.12 |
| Compound 1 | 0.29 |

What is claimed is:

1. A compound comprising the amino acid sequence of Formula (II):

Xaa$_1$ Xaa$_2$ Xaa$_3$ Gly Thr Xaa$_4$ Xaa$_5$ Xaa$_6$ Xaa$_7$ Xaa$_8$ Ser Lys Gln Xaa$_9$ Glu Glu Glu Ala Val Arg Leu Xaa$_{10}$ Xaa$_{11}$ Xaa$_{12}$ Xaa$_{13}$ Leu X$_1$ Gly Gly Xaa$_{14}$ Ser Ser Gly Ala Xaa$_{15}$ Xaa$_{16}$ Xaa$_{17}$ Xaa$_{18}$-Z;

wherein:
Xaa$_1$ 4-imidazopropionyl;
Xaa$_2$ is Ser, Gly, Ala or Thr;
Xaa$_3$ is Asp or Glu;
Xaa$_4$ is Phe, Tyr or naphthylalanine;
Xaa$_5$ is Thr or Ser;
Xaa$_6$ is Ser or Thr;
Xaa$_7$ is Asp or Glu;
Xaa$_8$ is Leu, Ile, Val, pentylglycine or Met;
Xaa$_9$ is Leu, Ile, pentylglycine, Val or Met;
Xaa$_{10}$ is Phe, Tyr or naphthylalanine;
Xaa$_{11}$ is Ile, Val, Leu, pentylglycine, tert-butylglycine or Met;
Xaa$_{12}$ is Glu or Asp;
Xaa$_{13}$ is Trp, Phe, Tyr, or naphthylalanine;
X$_1$ is Lys Asn, Asn Lys, Lys-NH$^e$-R Asn, or Asn Lys-NH$^e$-R where R is Lys, Arg, C$_1$-C$_{10}$ straight chain or branched alkanoyl or cycloalkyanoyl;
Xaa$_{14}$, Xaa$_{15}$, Xaa$_{16}$ and Xaa$_{17}$ are independently Pro, homoproline, 3Hyp, 4Hyp, thioproline, N-alkylglycine, N-alkylpentylglycine or N-alkylalanine;
Xaa$_{18}$ is Ser, Thr or Tyr; and
Z is —OH or —NH$_2$;
with the proviso that the compound does not have the formula of SEQ ID. NO:1 or 2.

2. The compound of claim 1, wherein:
Xaa$_2$ is Gly;
Xaa$_3$ is Glu;
Xaa$_4$ is Phe;
Xaa$_5$ is Thr;
Xaa$_6$ is Ser;
Xaa$_7$ is Asp;
Xaa$_8$ is Leu;
Xaa$_9$ is Leu or Met;
Xaa$_{10}$ is Phe;
Xaa$_{11}$ is Ile;
Xaa$_{12}$ is Glu;
Xaa$_{13}$ is Trp or Phe;
X$_1$ is Lys Asn;
Xaa$_{14}$, Xaa$_{15}$, Xaa$_{16}$ and Xaa$_{17}$ are independently Pro;
Xaa$_{18}$ is Ser; and
Z is —NH$_2$.

3. The compound of claim 2, wherein Xaa$_9$ is Met and Xaa$_{13}$ is Trp.

4. The compound of claim 2, wherein Xaa$_9$ is Len.

5. The compound of claim 4, wherein Xaa$_9$ is Len and Xaa$_{13}$ is Phe.

6. A pharmaceutical composition comprising a therapeutically effective amount of the compound of claim 1 and a pharmaceutically acceptable carrier.

7. A pharmaceutical composition comprising a therapeutically effective amount of the compound of claim 2 and a pharmaceutically acceptable carrier.

8. A pharmaceutical composition comprising a therapeutically effective amount of the compound of claim 3 and a pharmaceutically acceptable carrier.

9. A pharmaceutical composition comprising a therapeutically effective amount of the compound of claim 4 and a pharmaceutically acceptable carrier.

10. A pharmaceutical composition comprising a therapeutically effective amount of the compound of claim 5 and a pharmaceutically acceptable carrier.

\* \* \* \* \*

SEQUENCE LISTING

<160> NUMBER OF SEQ ID NOS: 41

<210> SEQ ID NO 1
<211> LENGTH: 39
<212> TYPE: PRT
<213> ORGANISM: Heloderma horridum
<220> FEATURE:
<223> OTHER INFORMATION: c-term amidation

<400> SEQUENCE: 1

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma suspectum
<220> FEATURE:
<223> OTHER INFORMATION: c-term amidation

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 30
<212> TYPE: PRT
<213> ORGANISM: Homo sapiens
<220> FEATURE:
<223> OTHER INFORMATION: c-term amidation

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Exendin
      agonist formula peptide
<220> FEATURE:
<223> OTHER INFORMATION: c-term may be amidated
<220> FEATURE:
<223> OTHER INFORMATION: see specification as filed for detailed
      description of substitutions and preferred embodiments
<220> FEATURE:
<221> NAME/KEY: MOD_RES
<222> LOCATION: (1)
<223> OTHER INFORMATION: His, Arg or Tyr
<220> FEATURE:
<221> NAME/KEY: MOD_RES
<222> LOCATION: (2)
<223> OTHER INFORMATION: Ser, Gly, Ala or Thr
<220> FEATURE:

```
<221> NAME/KEY: MOD_RES
<222> LOCATION: (3)
<223> OTHER INFORMATION: Asp or glu
<220> FEATURE:
<221> NAME/KEY: MOD_RES
<222> LOCATION: (6)
<223> OTHER INFORMATION: Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Leu, Ile, Val, pentylglycine or Met
<220> FEATURE:
<221> NAME/KEY: MOD_RES
<222> LOCATION: (14)
<223> OTHER INFORMATION: Leu, Ile, pentylglycine, Val or Met
<220> FEATURE:
<221> NAME/KEY: MOD_RES
<222> LOCATION: (22)
<223> OTHER INFORMATION: Phe, Tyr or naphthylalanine
<220> FEATURE:
<221> NAME/KEY: MOD_RES
<222> LOCATION: (23)
<223> OTHER INFORMATION: Ile, Val, Leu, pentylglycine, tert-butylglycine
      or Met
<220> FEATURE:
<221> NAME/KEY: MOD_RES
<222> LOCATION: (24)
<223> OTHER INFORMATION: Glu or Asp
<220> FEATURE:
<221> NAME/KEY: MOD_RES
<222> LOCATION: (25)
<223> OTHER INFORMATION: Trp, Phe, Tyr or naphthylalanine
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine, N-alkylpentylglycine and N-alkylalanine
<220> FEATURE:
<221> NAME/KEY: MOD_RES
<222> LOCATION: (36)..(38)
<223> OTHER INFORMATION: Pro, homoproline, 3Hyp, 4Hyp, thioproline,
      N-alkylglycine, N-alkylpentylglycine and N-alkylalanine
<220> FEATURE:
<221> NAME/KEY: MOD_RES
<222> LOCATION: (39)
<223> OTHER INFORMATION: Ser, Thr or Tyr

<400> SEQUENCE: 4

Xaa Xaa Xaa Gly Thr Xaa Xaa Xaa Xaa Xaa Ser Lys Gln Xaa Glu Glu
 1               5                  10                  15

Glu Ala Val Arg Leu Xaa Xaa Xaa Xaa Xaa Leu Lys Asn Gly Gly Xaa Ser
            20                  25                  30

Ser Gly Ala Xaa Xaa Xaa Xaa
        35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation
```

```
<400> SEQUENCE: 5

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 6

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 7

His Gly Glu Gly Thr Phe Thr Ser Asp Leu Ser Lys Gln Met Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 8

Tyr Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 9
```

```
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 9

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Tyr
        35

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 10

His Gly Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (6)
<223> OTHER INFORMATION: napthylalanine
<220> FEATURE:
<223> OTHER INFORMATION: c-term amidation

<400> SEQUENCE: 11

His Gly Glu Gly Thr Xaa Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 12
```

-continued

His Gly Glu Gly Thr Phe Ser Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 13

His Gly Glu Gly Thr Phe Ser Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 14

His Gly Glu Gly Thr Phe Thr Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 15

His Gly Glu Gly Thr Phe Thr Ser Glu Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 16
<211> LENGTH: 39
<212> TYPE: PRT

```
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (10)
<223> OTHER INFORMATION: pentylglycine
<220> FEATURE:
<223> OTHER INFORMATION: c-term amidation

<400> SEQUENCE: 16

His Gly Glu Gly Thr Phe Thr Ser Asp Xaa Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (10)
<223> OTHER INFORMATION: pentylglycine
<220> FEATURE:
<223> OTHER INFORMATION: c-term amidation

<400> SEQUENCE: 17

His Gly Glu Gly Thr Phe Thr Ser Asp Xaa Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (14)
<223> OTHER INFORMATION: pentylglycine
<220> FEATURE:
<223> OTHER INFORMATION: c-term amidation

<400> SEQUENCE: 18

His Gly Glu Gly Thr Phe Thr Ser Asp Leu Ser Lys Gln Xaa Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
```

```
<223> OTHER INFORMATION: Description of Artificial Sequence: Exendin
      agonist peptide
<220> FEATURE:
<223> OTHER INFORMATION: c-term amidation
<220> FEATURE:
<221> NAME/KEY: MOD_RES
<222> LOCATION: (14)
<223> OTHER INFORMATION: pentylglycine

<400> SEQUENCE: 19

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (22)
<223> OTHER INFORMATION: napthylalanine
<220> FEATURE:
<223> OTHER INFORMATION: c-term amidation

<400> SEQUENCE: 20

His Gly Glu Gly Thr Phe Thr Ser Asp Leu Ser Lys Gln Met Glu Glu
 1               5                  10                  15

Glu Ala Val Arg Leu Xaa Ile Glu Trp Leu Lys Asn Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 21

His Gly Glu Gly Thr Phe Thr Ser Asp Leu Ser Lys Gln Met Glu Glu
 1               5                  10                  15

Glu Ala Val Arg Leu Phe Val Glu Trp Leu Lys Asn Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 22
```

-continued

His Gly Glu Gly Thr Phe Thr Ser Asp Leu Ser Lys Gln Leu Glu Glu
1               5                   10                  15

Glu Ala Val Arg Leu Phe Val Glu Phe Leu Lys Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (23)
<223> OTHER INFORMATION: tert-butylglycine
<220> FEATURE:
<223> OTHER INFORMATION: c-term amidation

<400> SEQUENCE: 23

His Gly Glu Gly Thr Phe Thr Ser Asp Leu Ser Lys Gln Met Glu Glu
1               5                   10                  15

Glu Ala Val Arg Leu Phe Xaa Glu Trp Leu Lys Asn Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (23)
<223> OTHER INFORMATION: tert-butylglycine
<220> FEATURE:
<223> OTHER INFORMATION: c-term amidation

<400> SEQUENCE: 24

His Gly Glu Gly Thr Phe Thr Ser Asp Leu Ser Lys Gln Leu Glu Glu
1               5                   10                  15

Glu Ala Val Arg Leu Phe Xaa Glu Phe Leu Lys Asn Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Asp Trp Leu Lys Asn Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<223> OTHER INFORMATION: c-term amidation

<400> SEQUENCE: 26

His Gly Glu Gly Thr Phe Thr Ser Asp Leu Ser Lys Gln Met Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (31)
<223> OTHER INFORMATION: thioproline
<220> FEATURE:
<221> NAME/KEY: MOD_RES
<222> LOCATION: (36)..(38)
<223> OTHER INFORMATION: thioproline
<220> FEATURE:
<223> OTHER INFORMATION: c-term amidation

<400> SEQUENCE: 27

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa Ser
        35

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (36)..(38)
<223> OTHER INFORMATION: thioproline
<220> FEATURE:
<223> OTHER INFORMATION: c-term amidation

<400> SEQUENCE: 28

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa Ser

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (31)
<223> OTHER INFORMATION: homoproline
<220> FEATURE:
<221> NAME/KEY: MOD_RES
<222> LOCATION: (36)..(38)
<223> OTHER INFORMATION: homoproline
<220> FEATURE:
<223> OTHER INFORMATION: c-term amidation

<400> SEQUENCE: 29

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa Ser
        35

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (36)..(38)
<223> OTHER INFORMATION: homoproline
<220> FEATURE:
<223> OTHER INFORMATION: c-term amidation

<400> SEQUENCE: 30

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa Ser
        35

<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (31)
<223> OTHER INFORMATION: thioproline
<220> FEATURE:
<221> NAME/KEY: MOD_RES
<222> LOCATION: (36)..(38)
<223> OTHER INFORMATION: thioproline
<220> FEATURE:
<223> OTHER INFORMATION: c-term amidation

<400> SEQUENCE: 31

His Gly Glu Gly Thr Phe Thr Ser Asp Leu Ser Lys Gln Leu Glu Glu

```
                 1               5                  10                 15
Glu Ala Val Arg Leu Phe Ile Glu Phe Leu Lys Asn Gly Gly Xaa Ser
                20                  25                 30

Ser Gly Ala Xaa Xaa Xaa Ser
            35

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (31)
<223> OTHER INFORMATION: homoproline
<220> FEATURE:
<221> NAME/KEY: MOD_RES
<222> LOCATION: (36)..(38)
<223> OTHER INFORMATION: homoproline
<220> FEATURE:
<223> OTHER INFORMATION: c-term amidation

<400> SEQUENCE: 32

His Gly Glu Gly Thr Phe Thr Ser Asp Leu Ser Lys Gln Leu Glu Glu
  1               5                  10                 15

Glu Ala Val Arg Leu Phe Ile Glu Phe Leu Lys Asn Gly Gly Xaa Ser
                20                  25                 30

Ser Gly Ala Xaa Xaa Xaa Ser
            35

<210> SEQ ID NO 33
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (31)
<223> OTHER INFORMATION: N-methylalanine
<220> FEATURE:
<221> NAME/KEY: MOD_RES
<222> LOCATION: (36)..(38)
<223> OTHER INFORMATION: N-methylalanine
<220> FEATURE:
<223> OTHER INFORMATION: c-term amidation

<400> SEQUENCE: 33

His Gly Glu Gly Thr Phe Thr Ser Asp Leu Ser Lys Gln Met Glu Glu
  1               5                  10                 15

Glu Ala Val Arg Leu Phe Ile Glu Trp Leu Lys Asn Gly Gly Xaa Ser
                20                  25                 30

Ser Gly Ala Xaa Xaa Xaa Ser
            35

<210> SEQ ID NO 34
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (36)..(38)
<223> OTHER INFORMATION: N-methylalanine
```

```
<220> FEATURE:
<223> OTHER INFORMATION: c-term amidation

<400> SEQUENCE: 34

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Xaa Xaa Xaa Ser
             35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (31)
<223> OTHER INFORMATION: N-methylalanine
<220> FEATURE:
<221> NAME/KEY: MOD_RES
<222> LOCATION: (36)..(38)
<223> OTHER INFORMATION: N-methylalanine
<220> FEATURE:
<223> OTHER INFORMATION: c-term amidation

<400> SEQUENCE: 35

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Xaa Ser
             20                  25                  30

Ser Gly Ala Xaa Xaa Xaa Ser
             35

<210> SEQ ID NO 36
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (1)
<223> OTHER INFORMATION: 4-Imidazolylpropionyl
<220> FEATURE:
<221> NAME/KEY: MOD_RES
<222> LOCATION: (27)
<223> OTHER INFORMATION: Lys-NH(epsilon) octanoyl
<220> FEATURE:
<223> OTHER INFORMATION: c-term amidation

<400> SEQUENCE: 36

Xaa Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Pro Ser
             35

<210> SEQ ID NO 37
<211> LENGTH: 39
<212> TYPE: PRT
<213> ORGANISM: Artificial Sequence
<220> FEATURE:
```

```
<223> OTHER INFORMATION: Description of Artificial Sequence: Exendin
      agonist peptide
<220> FEATURE:
<221> NAME/KEY: MOD_RES
<222> LOCATION: (1)
<223> OTHER INFORMATION: 4-Imidazolylpropionyl
<220> FEATURE:
<221> NAME/KEY: MOD_RES
<222> LOCATION: (27)
<223> OTHER INFORMATION: Lys-NH(epsilon) octanoyl
<220> FEATURE:
<223> OTHER INFORMATION: c-term amidation

<400> SEQUENCE: 37

Xaa Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
            35

<210> SEQ ID NO 38
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (1)
<223> OTHER INFORMATION: 4-Imidazolylpropionyl
<220> FEATURE:
<221> NAME/KEY: MOD_RES
<222> LOCATION: (28)
<223> OTHER INFORMATION: Lys-NH(epsilon) octanoyl
<220> FEATURE:
<223> OTHER INFORMATION: c-term amidation

<400> SEQUENCE: 38

Xaa Gly Glu Gly Thr Phe Thr Ser Asp Leu Ser Lys Gln Met Glu Glu
 1               5                  10                  15

Glu Ala Val Arg Leu Phe Ile Glu Trp Leu Asn Lys Gly Gly Pro Ser
            20                  25                  30

Ser Gly Ala Pro Pro Pro Ser
            35

<210> SEQ ID NO 39
<211> LENGTH: 39
<212> TYPE: PRT
<213> ORGANISM: Artificial Sequence
<220> FEATURE:
<223> OTHER INFORMATION: Description of Artificial Sequence: Exendin
      agonist peptide
<220> FEATURE:
<221> NAME/KEY: MOD_RES
<222> LOCATION: (1)
<223> OTHER INFORMATION: 4-Imidazolylpropionyl
<220> FEATURE:
<221> NAME/KEY: MOD_RES
<222> LOCATION: (28)
<223> OTHER INFORMATION: Lys-NH(epsilon) octanoyl
<220> FEATURE:
<223> OTHER INFORMATION: c-term amidation

<400> SEQUENCE: 39

Xaa Gly Glu Gly Thr Phe Thr Ser Asp Leu Ser Lys Gln Leu Glu Glu
 1               5                  10                  15

Glu Ala Val Arg Leu Phe Ile Glu Phe Leu Asn Lys Gly Gly Pro Ser
            20                  25                  30
```

Ser Gly Ala Pro Pro Pro Ser
        35

<210> SEQ ID NO 40
<211> LENGTH: 40
<212> TYPE: PRT
<213> ORGANISM: Artificial Sequence
<220> FEATURE:
<223> OTHER INFORMATION: Description of Artificial Sequence: Exendin
      agonist formula peptide
<220> FEATURE:
<223> OTHER INFORMATION: c-term may be amidated
<220> FEATURE:
<223> OTHER INFORMATION: see specification as filed for detailed
      description of substitutions and preferred embodiments
<220> FEATURE:
<221> NAME/KEY: MOD_RES
<222> LOCATION: (1)
<223> OTHER INFORMATION: His, Arg, Tyr or 4-imidazopropionyl
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Asp or Glu
<220> FEATURE:
<221> NAME/KEY: MOD_RES
<222> LOCATION: (6)
<223> OTHER INFORMATION: Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Leu, Ile, Val, pentylglycine or Met
<220> FEATURE:
<221> NAME/KEY: MOD_RES
<222> LOCATION: (14)
<223> OTHER INFORMATION: Leu, Ile, pentylglycine, Val or Met
<220> FEATURE:
<221> NAME/KEY: MOD_RES
<222> LOCATION: (22)
<223> OTHER INFORMATION: Phe, Tyr or naphthylalanine
<220> FEATURE:
<221> NAME/KEY: MOD_RES
<222> LOCATION: (23)
<223> OTHER INFORMATION: Ile, Val, Leu, pentylglycine, tert-
      butylglycine or Met
<220> FEATURE:
<221> NAME/KEY: MOD_RES
<222> LOCATION: (24)
<223> OTHER INFORMATION: Glu or Asp
<220> FEATURE:
<221> NAME/KEY: MOD_RES
<222> LOCATION: (25)
<223> OTHER INFORMATION: Trp, Phe, Tyr or naphthylalanine
<220> FEATURE:
<221> NAME/KEY: MOD_RES
<222> LOCATION: (27)..(29)
<223> OTHER INFORMATION: Lys Asn, Asn Lys, Lys-NH(epsilon)-Lys-Asn,
      Lys-NH(epsilon)-Arg-Asn or Lys-NH(epsilon)-Lys or Lys-NH(epsilon)-
      Arg; this range may encompass 2-3 residues according to the
      specification as filed
<220> FEATURE:
<221> NAME/KEY: MOD_RES
<222> LOCATION: (32)

```
<223> OTHER INFORMATION: Pro, homoproline, 3Hyp, 4Hyp, thioproline,
      N-alkylglycine, N-alkylpentylglycine and N-alkylalanine
<220> FEATURE:
<221> NAME/KEY: MOD_RES
<222> LOCATION: (37)..(39)
<223> OTHER INFORMATION: Pro, homoproline, 3Hyp, 4Hyp, thioproline,
      N-alkylglycine, N-alkylpentylglycine and N-alkylalanine
<220> FEATURE:
<221> NAME/KEY: MOD_RES
<222> LOCATION: (40)
<223> OTHER INFORMATION: Ser, Thr or Tyr
<220> FEATURE:
<223> OTHER INFORMATION: this sequence may encompass 39-40 residues
      according to the substitutions described above

<400> SEQUENCE: 40

Xaa Xaa Xaa Gly Thr Xaa Xaa Xaa Xaa Xaa Ser Lys Gln Xaa Glu Glu
 1               5                  10                  15

Glu Ala Val Arg Leu Xaa Xaa Xaa Xaa Leu Xaa Xaa Xaa Gly Gly Xaa
            20                  25                  30

Ser Ser Gly Ala Xaa Xaa Xaa Xaa
        35                  40

<210> SEQ ID NO 41
<211> LENGTH: 39
<212> TYPE: PRT
<213> ORGANISM: Artificial Sequence
<220> FEATURE:
<223> OTHER INFORMATION: Description of Artificial Sequence: Exendin
      agonist formula peptide
<220> FEATURE:
<223> OTHER INFORMATION: c-term may be amidated
<220> FEATURE:
<223> OTHER INFORMATION: see specification as filed for detailed
      description of substitutions and preferred embodiments
<220> FEATURE:
<221> NAME/KEY: MOD_RES
<222> LOCATION: (1)
<223> OTHER INFORMATION: His or Arg
<220> FEATURE:
<221> NAME/KEY: MOD_RES
<222> LOCATION: (2)
<223> OTHER INFORMATION: Gly or Ala
<220> FEATURE:
<221> NAME/KEY: MOD_RES
<222> LOCATION: (3)
<223> OTHER INFORMATION: Asp or glu
<220> FEATURE:
<221> NAME/KEY: MOD_RES
<222> LOCATION: (6)
<223> OTHER INFORMATION: Phe or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Leu or pentylglycine
<220> FEATURE:
<221> NAME/KEY: MOD_RES
<222> LOCATION: (14)
```

```
<223> OTHER INFORMATION: Leu or pentylglycine
<220> FEATURE:
<221> NAME/KEY: MOD_RES
<222> LOCATION: (22)
<223> OTHER INFORMATION: Phe or naphthylalanine
<220> FEATURE:
<221> NAME/KEY: MOD_RES
<222> LOCATION: (23)
<223> OTHER INFORMATION: Ile, Val or tert-butylglycine
<220> FEATURE:
<221> NAME/KEY: MOD_RES
<222> LOCATION: (24)
<223> OTHER INFORMATION: Glu or Asp
<220> FEATURE:
<221> NAME/KEY: MOD_RES
<222> LOCATION: (25)
<223> OTHER INFORMATION: Trp or Phe
<220> FEATURE:
<221> NAME/KEY: MOD_RES
<222> LOCATION: (31)
<223> OTHER INFORMATION: Pro, homoproline, thioproline or
      N-methylalanine
<220> FEATURE:
<221> NAME/KEY: MOD_RES
<222> LOCATION: (36)..(38)
<223> OTHER INFORMATION: Pro, homoproline, thioproline or
      N-methylalanine
<220> FEATURE:
<221> NAME/KEY: MOD_RES
<222> LOCATION: (39)
<223> OTHER INFORMATION: Ser or Thr

<400> SEQUENCE: 41

Xaa Xaa Xaa Gly Thr Xaa Xaa Xaa Xaa Xaa Ser Lys Gln Xaa Glu Glu
 1               5                  10                  15

Glu Ala Val Arg Leu Xaa Xaa Xaa Xaa Leu Lys Asn Gly Gly Xaa Ser
             20                  25                  30

Ser Gly Ala Xaa Xaa Xaa Xaa
             35
```